(12) United States Patent
He

(10) Patent No.: US 11,517,262 B2
(45) Date of Patent: Dec. 6, 2022

(54) MONITOR EQUIPMENT

(71) Applicant: Kongyuan He, Encinco, CA (US)

(72) Inventor: Kongyuan He, Encinco, CA (US)

( * ) Notice: Subject to any disclaimer, the term of this patent is extended or adjusted under 35 U.S.C. 154(b) by 712 days.

(21) Appl. No.: 16/542,781

(22) Filed: Aug. 16, 2019

(65) Prior Publication Data
US 2020/0060619 A1    Feb. 27, 2020

Related U.S. Application Data

(60) Provisional application No. 62/722,009, filed on Aug. 23, 2018.

(51) Int. Cl.
*A61B 5/00* (2006.01)
*A61B 18/14* (2006.01)
*A61M 5/315* (2006.01)
*G16H 15/00* (2018.01)
*G16H 20/17* (2018.01)
*A61B 5/01* (2006.01)
*A61B 5/1455* (2006.01)
*A61B 5/021* (2006.01)
*A61B 18/00* (2006.01)

(52) U.S. Cl.
CPC .......... *A61B 5/6838* (2013.01); *A61B 5/6819* (2013.01); *A61B 18/14* (2013.01); *A61M 5/31568* (2013.01); *G16H 15/00* (2018.01); *G16H 20/17* (2018.01); *A61B 5/01* (2013.01); *A61B 5/02141* (2013.01); *A61B 5/1455* (2013.01); *A61B 2018/00601* (2013.01)

(58) Field of Classification Search
CPC ..... A61B 5/6838; A61B 5/6819; A61B 18/14; A61B 5/01; A61B 5/02141; A61B 5/1455; A61B 2018/00601; A61B 5/022; A61B 2505/05; A61B 18/1206; A61B 2018/00916; A61M 5/31568; G16H 15/00; G16H 20/17
See application file for complete search history.

(56) References Cited

U.S. PATENT DOCUMENTS

| | | | | |
|---|---|---|---|---|
| 2001/0051766 A1* | 12/2001 | Gazdzinski | ............ | A61B 10/02 606/1 |
| 2004/0092992 A1* | 5/2004 | Adams | ............ | A61B 17/32002 606/180 |
| 2009/0015558 A1* | 1/2009 | Hung | ................. | A61B 5/02416 345/163 |
| 2013/0276785 A1* | 10/2013 | Melker | ................ | A61B 5/0205 128/204.23 |
| 2015/0335288 A1* | 11/2015 | Toth | ..................... | A61B 5/6833 600/391 |
| 2017/0266443 A1* | 9/2017 | Rajguru | .................. | A61B 5/24 |

* cited by examiner

*Primary Examiner* — Unsu Jung
*Assistant Examiner* — Natasha Patel
(74) *Attorney, Agent, or Firm* — Dhiraj Jindal; Patent Yogi LLC

(57) ABSTRACT

Disclosed is a monitor equipment. The monitor equipment comprising a nasal clip configured to clip onto nasal septum of a patient. Further, the monitor equipment comprising a monitor detector connected to the nasal clip through at least one of a wired and a wireless connection. Further, the monitor equipment comprising an electro-surgical unit (ESU) connected to the monitor detector through at least one of a wired and a wireless connection

17 Claims, 6 Drawing Sheets

MONITOR EQUIPMENT

RELATED APPLICATION(S)

Under provisions of 35 U.S.C. § 119e, the Applicant(s) claim the benefit of U.S. provisional application No. 62/722,009, filed on Aug. 23, 2018, which is incorporated herein by reference.

FIELD OF THE INVENTION

The invention relates generally to medical and surgical devices and equipment, and in particular to improvements for an electro-surgical unit (ESU) and exact monitoring.

BACKGROUND OF THE INVENTION

Modern surgery relies heavily on electronic devices. In surgeries to cut, coagulate, dissect, fulgurate, ablate, and decrease tissue, the electro-surgical unit (ESU) has become a routine equipment item to reduce blood loss, which leads to more rapid recovery. However, the vital signs (VS) monitoring is vulnerable to unintentional interference from ESU and human activity by the patient or the surgical staff. Furthermore, concerns have been raised in the medical community regarding electric medical records and medical research, as well as clinic quality management.

For example, during new drug clinical research on surgical patients, copy-and-paste or record cloning can be done from standard guideline or protocols. A missed edit from "positive result" to "negative result" can have devastating effects on not only a patient's record, but also on the patient's treatment and the reports of medical researchers as well as quality control of the research. For example, during a clinical observation of a new drug administration during a surgery, on the monitor screen, a patient's significant decline in blood pressure with arrhythmia after the physician administered the new drug about one minute later, at the same time the ESU was active or others, can support a management decision which can be made after the ESU is deactivated, which will obtain a reliable record for study and review.

Accordingly, there is a need for an improved surgical equipment and VS monitor that may overcome one or more of the abovementioned problems and/or limitations.

SUMMARY OF THE INVENTION

This summary is provided to introduce a selection of concepts in a simplified form that are further described below in the Detailed Description. This summary is not intended to identify key features or essential features of the claimed subject matter. Nor is this summary intended to be used to limit the claimed subject matter's scope.

According to some embodiments, the present disclosure relates to a monitor equipment. The monitor equipment comprising a nasal clip configured to clip onto nasal septum of a patient. Further, the monitor equipment comprising a monitor detector connected to the nasal clip through at least one of a wired and a wireless connection. The monitor detector may be a vital signs (VS) monitor. Further, the monitor equipment comprising an electro-surgical unit (ESU) connected to the monitor detector through at least one of a wired and a wireless connection.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAILED DESCRIPTION OF THE INVENTION

Figure 1:
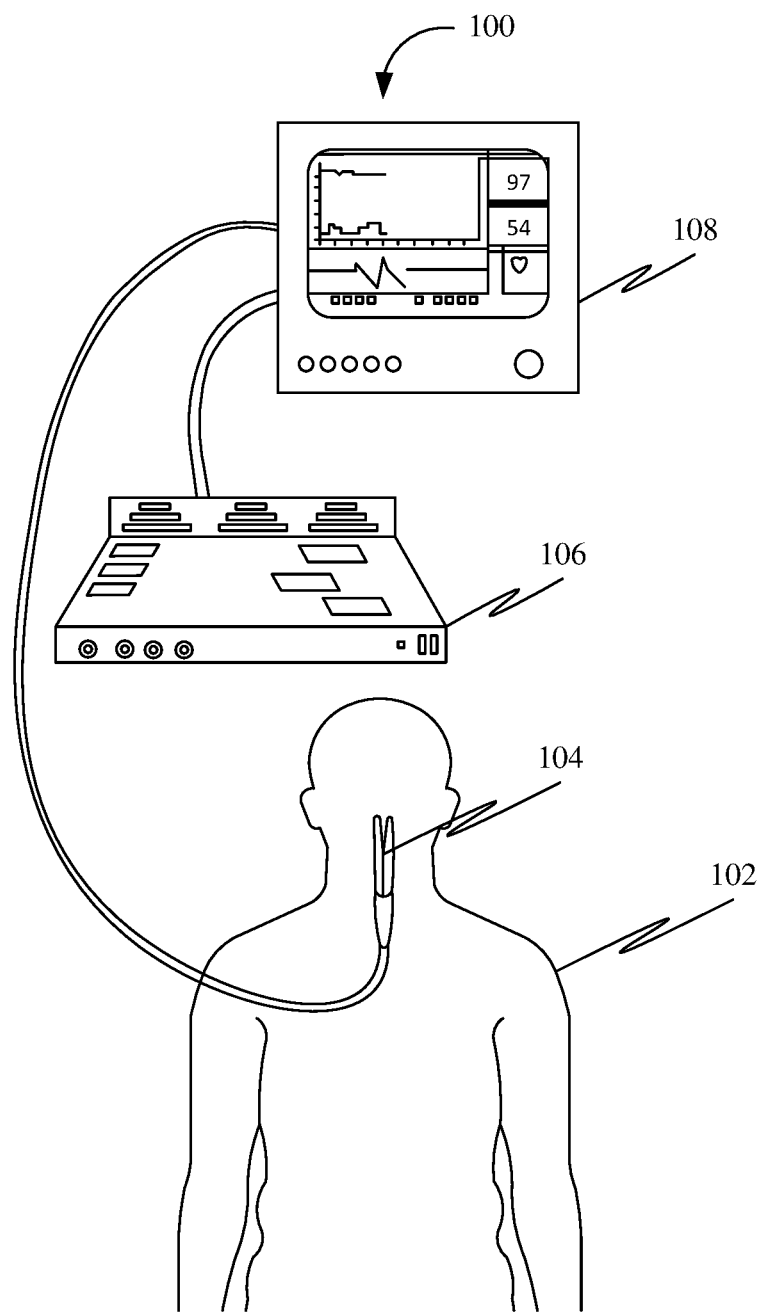
FIG. 1 is a top view of a patient with a nasal clip, an ESU and a monitor detector, in accordance with an exemplary embodiment.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

The present disclosure includes many aspects and features. Moreover, while many aspects and features relate to, and are described in, the context of surgical equipment, embodiments of the present disclosure are not limited to use only in this context.

Overview:

According to some embodiments, the present disclosure may be directed to improvements for an electro-surgical unit (ESU) or a monitor unit. An internal switch is added which sends an image or signal from the ESU generator to the monitor screen. An improved pulse oximeter (POx) and temperature clip is further provided, which may be affixed to the nasal septum of the patient. This measures both oxygen (O2) saturation and "near" core temperature. One or two integrated motion sensors are provided, which may be placed on the patient. Pressure sensors in the sphygmomanometer cuff, as well as a hardware extension around the cuff, are provided which protect the accuracy and reliability of blood pressure readings.

Further, the disclosure may be directed to a series of improvements for an electro-surgical unit and real time evidence of management, which protect the monitor from the ESU and human interference and provide more reliable medical readings and records during surgery, provide a reliable medical record and/or research report.

Figure 2:
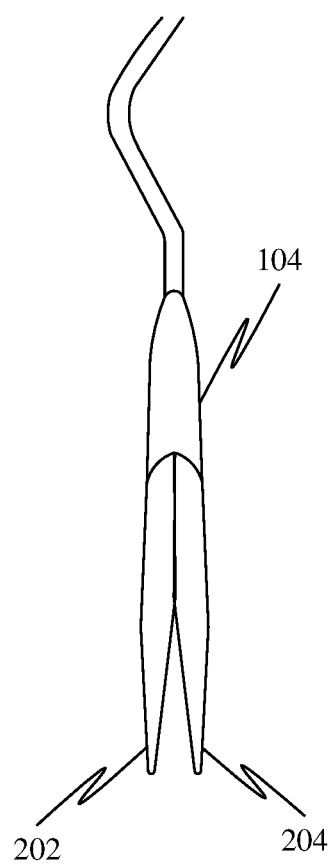
FIG. 2 is a top view of the nasal clip, in accordance with an exemplary embodiment.
Figure 3:
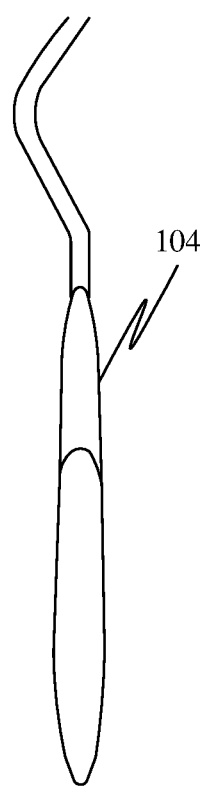
FIG. 3 is a side view of the nasal clip, in accordance with an exemplary embodiment.

FIG. 1 is a top view of a patient 102 with monitor equipment 100 comprising a nasal clip 104, an electro-surgical unit (ESU) 106 and a monitor detector 108, in accordance with an exemplary embodiment. FIG. 2 is a top view of the nasal clip 104. FIG. 3 is a side view of the nasal clip 104.

The nasal clip 104 may be configured to clip onto nasal septum of a patient 102. Further, the nasal clip 104 may include two probes 202-204 inserted in the nasal cavities of the patient 1. Further, ends of the two probes 202-204 may touch a surface of the nasal septum of the patient 102. Further, at least one side of a probe in the two probes 202-204 includes at least one of a temperature sensor and a part of pulse oximeter (POx) sensor.

Further, the ESU 106 may include at least one of a generator, a handpiece and a foot switch, wherein at least one of the handpiece and the foot switch includes an on/off switch to control the ESU. Further, the at least one of the handpiece and the foot switch may include an internal switch, wherein when the on/off switch is activated, the internal switch is also activated. Further, the internal switch may be configured to send at least one of an image or a signal from the generator to the monitor.

Further, the monitor detector 108 may be connected to the nasal clip 104 through at least one of a wired and a wireless connection. Yet further, the monitor detector 108 connected to the ESU through at least one of a wired and a wireless connection. Further, the monitor may display the signal differently from any other information displayed on the monitor. Yet further, the monitor may display the signal using at least one of a differently colored wave form and a differently colored screen background.

Figure 4:
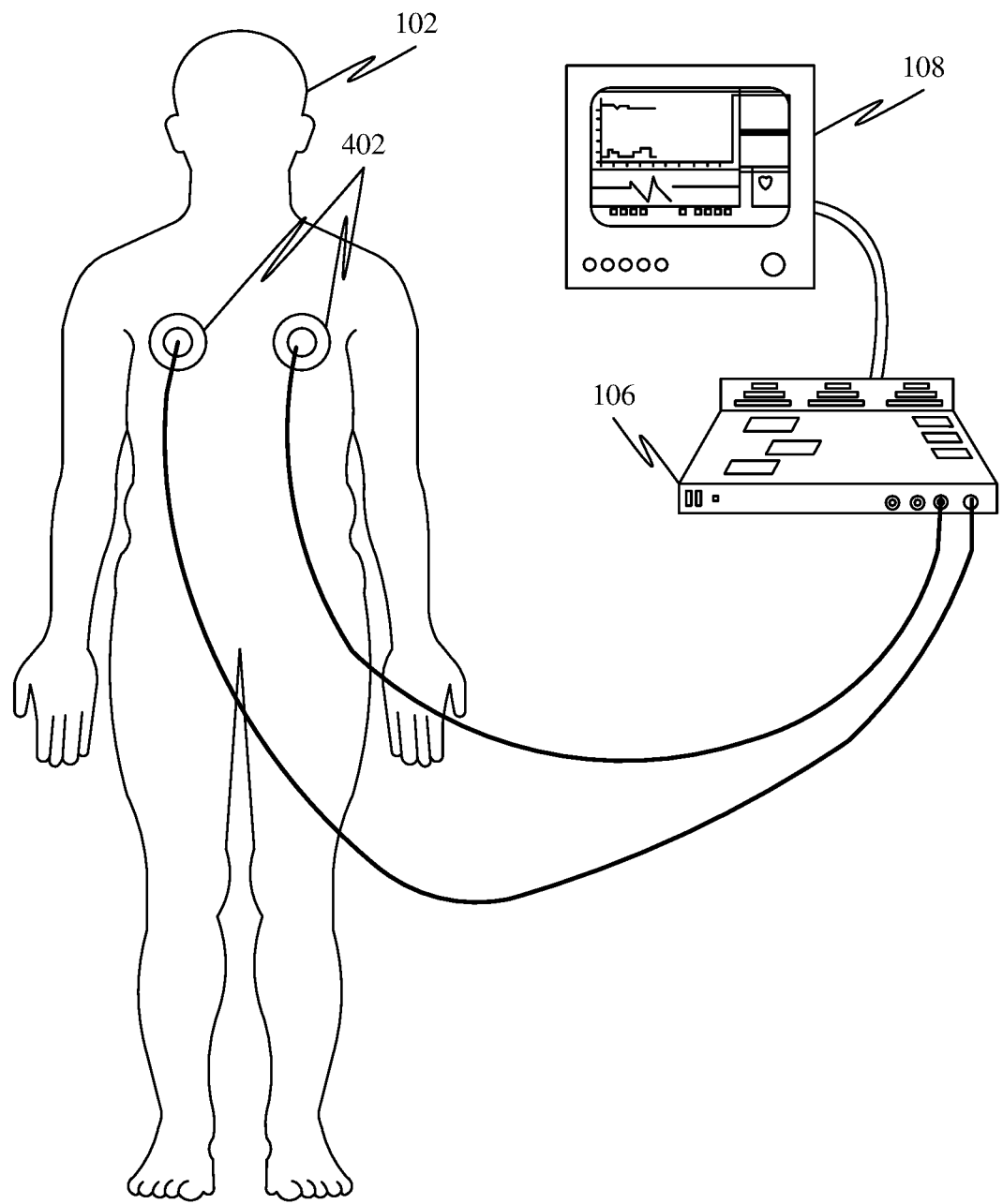
FIG. 4 is a top view of the patient with motion sensors placed on the chest of the patient, in accordance with an exemplary embodiment.

FIG. 4 is a top view of the patient 102 with at least one motion sensor 402 placed on the chest of the patient 102, in accordance with an exemplary embodiment. Further the at least one motion sensor 402 may be connected to the monitor detector and/or ESU. Further, the at least one motion sensor 402 may be configured to detect outside interference. Accordingly, the monitor equipment 100 may include the at least one motion sensor 402.

Figure 5:
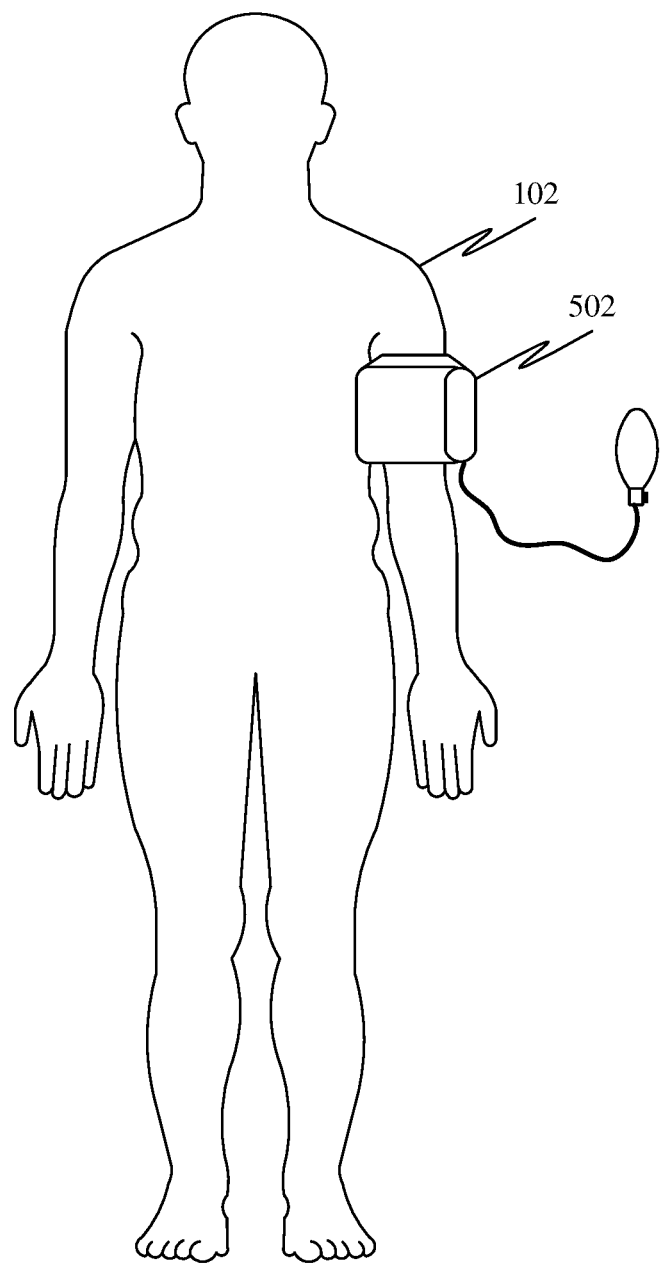
FIG. 5 is a top view of the patient with a cuff shell placed on a cuff of an arm of the patient, in accordance with an exemplary embodiment.

FIG. 5 is a top view of the patient 102 with a cuff shell 502 placed on a cuff of an arm of the patient 102, in accordance with an exemplary embodiment. Further, the cuff shell 502 may be placed over sphygmomanometer cuff. The sphygmomanometer cuff may be part of a blood pressure measuring equipment. Yet further, the cuff shell 502 may include pressure sensors configured to detect any external pressure applied on the cuff shell. Further, the cuff shell 502 may include a hardware extension configured to prevent any external pressure from being applied on the arm of the patient 102. Accordingly, the monitor equipment 100 may include the cuff shell 502.

Figure 6:
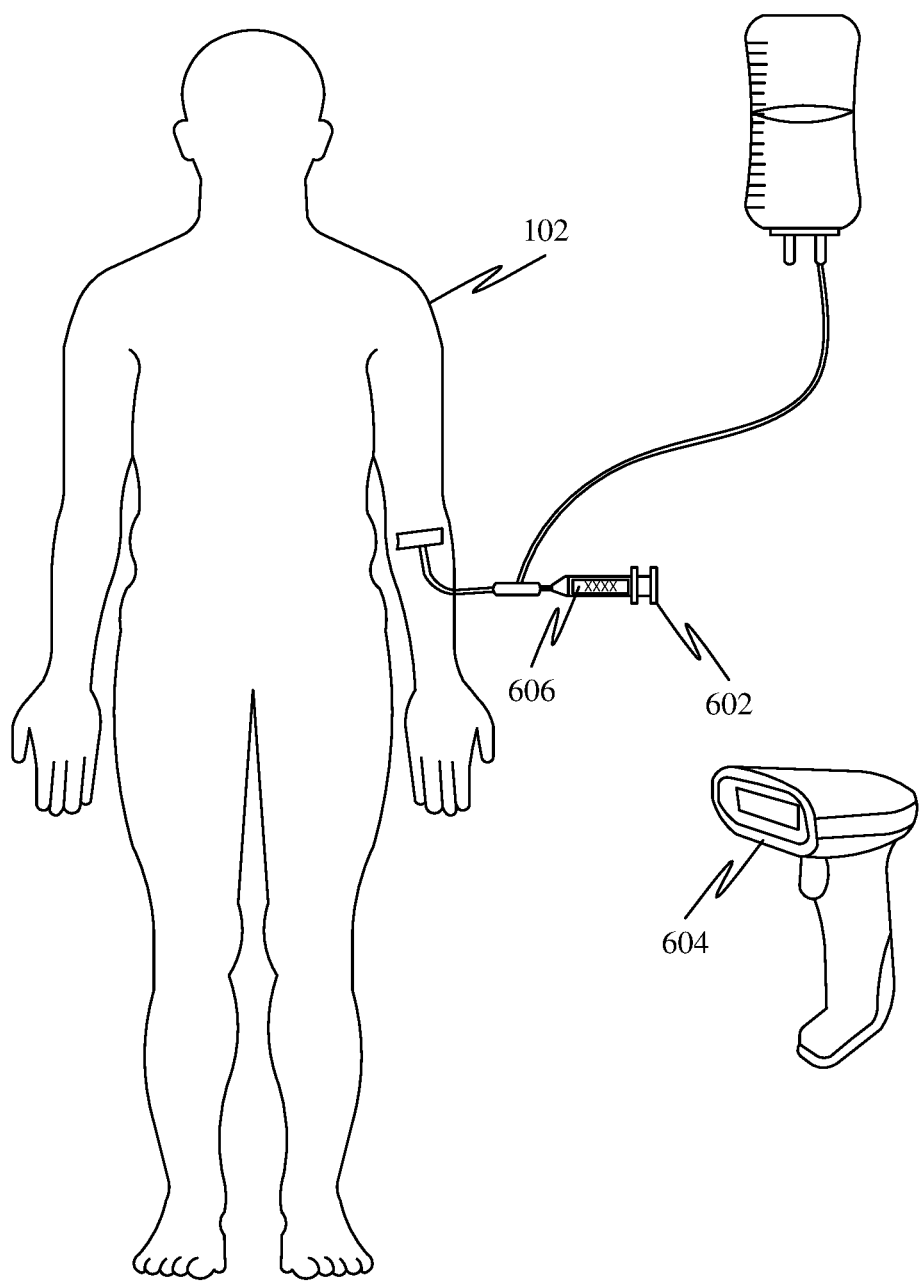
FIG. 6 is a top view of the patient with a syringe injecting medicine via Intravenous (IV) therapy and a scanner, in accordance with an exemplary embodiment.

FIG. 6 is a top view of the patient 102 with a syringe 602 injecting medicine via Intravenous (IV) therapy and a scanner 604 configured to scan a medication label 606 on the syringe 602, in accordance with an exemplary embodiment. Further, the scanner may use image recognition to measure the volume changes of dosage in the syringe 602. Yet further, the scanner 604 may be configured to calculate the dosage injected based on the measured volume changes. Moreover, the scanner 604 may include a display device to display the dosage injected and the injection time. Further, the scanner 604 may include a communication device to transmit a signal related to the dosage and injection time to a user device. For example, the user device may be at least one of instrument for monitoring recorder, a computer, or connect to a smartphone, a tablet or a smart watch. Accordingly, the monitor equipment 100 may include the syringe 602 and the scanner 604.

According to some embodiments, the disclosure is related to a series of mechanical and electronic improvements for existing surgical and monitor equipment. In the operating room, surgical instruments cause the most common interferences in the electrocardiogram (EKG) monitor. In surgery to cut, coagulate, dissect, fulgurate, ablate, and decrease tissue, the ESU 106 is used routinely to decrease blood loss. The ESU 106 may consist of a generator and a handpiece. The device is controlled using an on/off switch on the handpiece, or using a foot switch.

According to some embodiments, the present disclosure adds an internal switch to the handpiece or foot switch, such that when the on/off switch is activated, the internal switch is also activated. The internal switch may send an image or signal from the ESU generator to the monitor screen. The ESU generator's signals can be transmitted by a wired or wireless device, and may be displayed differently, such as using a differently colored wave form or differently colored screen background, such that the generator's signals may be easily distinguished from the current display features of the ESU.

Further, interference on the pulse oximeter (POx) may be caused by the POx sensor clip contacting the patient's skin in an abnormal way. The disclosure provides the POx and temperature sensor nasal clip 104 affixed to the nasal septum of the patient 102. This measures both oxygen (02) saturation and "near" core temperature.

The purpose of the nasal clip 104 is to decrease motion interferences with the oximeter function. The pulse oximeter nasal clip 104 may provide a plurality of special shapes, which may be clipped on the nasal septum to obtain near core temperature monitoring. The nasal septum location is closer to the core temperature, and will provide better temperature monitoring than the skin temperature. The nasal clip 104 is designed by using a nasal septum clipper, with the temperature probe embedded in the clipper tip end. It will contact nasal mucus to measure temperature. The nasal clip 104 may hold a single probe, or combine functions of a temperature probe and pulse oximeter probe.

Further, interference may also be caused by the patient's motion, such as breathing or trembling, or by the surgical staff, such as the surgeon sawing through a bone with an electric saw. This is frequently interpreted as ventricular tachycardia on the EKG. The present disclosure provides one or two integrated motion sensors 402 to be placed on the patient 102. This enables the user to distinguish actual physiological recordings from outside interference, which is necessary for electronic medical record keeping.

A common source of interference with the blood pressure reading occurs when a caregiver inadvertently leans on the cuff of the sphygmomanometer during the procedure, which may cause a change in the reading. This may be identified by observation, but there is currently no method of automatic documentation for the medical records. The disclosure teaches embedding pressure sensors in the cuff, to monitor any external pressure that may be applied, and a hardware extension placed around the cuff to prevent any external pressure from being applied.

According to some embodiments, the disclosure prevents external pressure on the blood pressure monitoring apparatus, by providing a cuff shell 502 which is preferably manufactured from a rigid, durable, easily cleaned material with a small degree of flexibility, such as plastic. Further, the cuff shell may be disposed after use. The cuff shell 502 may significantly wider than the sphygmomanometer cuff, and the diameter can be adjusted based on the patient's extremity size. The cuff shell 502 may maintain a consistent space between the inside of the cuff shell 502 and outer surface of the cuff of the sphygmomanometer. The space may be maintained by two inflatable air sacs, one at the upper edge of the cuff shell 502 and the other one at the lower edge.

According to some embodiments, the disclosure provides reliable real-time medical treatment information for intravenous administration. One purpose is to record the medication as it is administrated with the injection syringe 602. Further, the scanner 604 may be used to scan a medication label 606 on the syringe 602. The scanner 604 may use image recognition technology to measure the volume changes and time of the injection. For example, before injection, the image of the syringe 602 may show 10 ml of liquid volume, after the administration the image of the syringe 604 may show 6 ml. The scanner 604 may provide a mobile application which can calculate the dosage injected. The scanner 604 may further combine the functions of bar code scanning, image recognition and dosage calculation. The information of the IV medication injection, may be transmitted to medical recorder wired or wireless.

To use the disclosed monitor equipment 100, the user may affix the nasal clip 104 to the nasal septum of the patient 102, and the at least one motion sensor 402 to the chest of the patient 102. The user may apply the cuff shell 502 to the sphygmomanometer cuff, and create a scanned and photographic record of injected medications which are administered, using the scanner 604. Further operation is consistent with conventional operation of an ESU and monitors.

The nasal clip 104 and the at least one motion sensor 402 may be manufactured from flexible, durable materials, such as spring steel, nylon, and plastic. The cuff shell 502 may be manufactured from a rigid, durable material with a small degree of flexibility, such as plastic. The scanner 604 may be manufactured from rigid, durable materials, such as plastic, steel, copper alloy, and ceramics.

Components, component sizes, and materials listed above are preferable, but artisans will recognize that alternate components and materials could be selected without altering the scope of the invention.

Although the invention has been explained in relation to its preferred embodiment, it is to be understood that many other possible modifications and variations can be made without departing from the spirit and scope of the invention.

What is claimed is:

1. A monitor equipment comprising:
    a nasal clip configured to clip onto nasal septum of a patient;
    a monitor detector connected to the nasal clip through at least one of a wired and a wireless connection; and
    an electro-surgical unit (ESU) connected to the monitor detector through at least one of a wired and a wireless connection, wherein the ESU comprises a generator and at least one of a handpiece and a foot switch, wherein the at least one of the handpiece and the foot switch includes an on/off switch to control the ESU, wherein the at least one of the handpiece and the foot switch includes an internal switch, wherein when the on/off switch is activated, the internal switch is also activated, wherein the internal switch is configured to send at least one of an image and a signal from the generator to the monitor detector.

2. The monitor equipment of claim 1 wherein the nasal clip comprising two probes configured to be inserted in the nasal cavities of the patient, wherein ends of the two probes configured to touch a surface of the nasal septum of the patient.

3. The monitor equipment of claim 2 wherein at least one side of a probe in the two probes includes at least one of a temperature sensor and a part of a pulse oximeter (POx) sensor.

4. The monitor equipment of claim 1 wherein the monitor detector displays the signal differently from any other information displayed on the monitor detector.

5. The monitor equipment of claim 4 wherein the monitor detector displays the signal using at least one of a differently colored wave form and a differently colored screen background.

6. The monitor equipment of claim 1 further comprising at least one motion sensor to be placed on the patient, wherein the at least one motion sensor is connected to the ESU.

7. The monitor equipment of claim 6 wherein the at least one motion sensor is configured to be placed on the chest of the patient.

8. The monitor equipment of claim 6 wherein the at least one motion sensor is configured to detect outside interference.

9. The monitor equipment of claim 1 further comprising a cuff shell to be placed on a cuff of an arm of the patient.

10. The monitor equipment of claim 9 wherein the cuff shell is placed over sphygmomanometer cuff.

11. The monitor equipment of claim 9 wherein the cuff shell includes pressure sensors configured to detect any external pressure applied on the cuff shell.

12. The monitor equipment of claim 11 wherein the cuff shell includes a hardware extension configured to prevent any external pressure from being applied on the arm of the patient.

13. The monitor equipment of claim 1 further comprising a scanner configured to scan a medication label on a syringe.

14. The monitor equipment of claim 13 wherein the scanner uses image recognition to measure the volume changes of dosage in the syringe.

15. The monitor equipment of claim 14 wherein the scanner is configured to calculate the dosage injected based on the measured volume changes.

16. The monitor equipment of claim 15 wherein the scanner includes a display device to display the dosage injected.

17. The monitor equipment of claim 15 wherein the scanner includes a communication device configured to transmit a signal related to at least one of the dosage injected and an injection time to a user device.

* * * * *